(12) United States Patent
Inanc et al.

(10) Patent No.: US 9,599,743 B2
(45) Date of Patent: Mar. 21, 2017

(54) DENSITY MEASUREMENTS USING DETECTORS ON A PULSED NEUTRON MEASUREMENT PLATFORM

(71) Applicants: Feyzi Inanc, Spring, TX (US); David M. Chace, Houston, TX (US); Maxim Vasilyev, The Woodlands, TX (US); Sandeep S. Gade, Spring, TX (US); Steven M. Bliven, Houston, TX (US)

(72) Inventors: Feyzi Inanc, Spring, TX (US); David M. Chace, Houston, TX (US); Maxim Vasilyev, The Woodlands, TX (US); Sandeep S. Gade, Spring, TX (US); Steven M. Bliven, Houston, TX (US)

(73) Assignee: BAKER HUGHES INCORPORATED, Houston, TX (US)

( * ) Notice: Subject to any disclaimer, the term of this patent is extended or adjusted under 35 U.S.C. 154(b) by 0 days.

(21) Appl. No.: 14/699,910

(22) Filed: Apr. 29, 2015

(65) Prior Publication Data
US 2016/0320523 A1    Nov. 3, 2016

(51) Int. Cl.
*G01N 9/24* (2006.01)
*G01V 5/14* (2006.01)
*G01V 5/10* (2006.01)
*G01V 5/12* (2006.01)
*G01T 1/208* (2006.01)

(52) U.S. Cl.
CPC .............. *G01V 5/145* (2013.01); *G01N 9/24* (2013.01); *G01T 1/208* (2013.01); *G01V 5/102* (2013.01); *G01V 5/12* (2013.01)

(58) Field of Classification Search
CPC .......... G01V 5/145; G01V 5/102; G01V 5/12; G01N 9/24; G01T 1/208
See application file for complete search history.

(56) References Cited

U.S. PATENT DOCUMENTS

| 3,566,117 | A | * | 2/1971 | Tixier | .......................... 250/264 |
| 4,008,392 | A | * | 2/1977 | Lock | ..................... G01V 5/102 |
|  |  |  |  |  | 250/253 |
| 5,359,195 | A |  | 10/1994 | Gartner et al. |  |

(Continued)

OTHER PUBLICATIONS

Albertin, et al. "The Many Facets of Pulsed Neutron Cased-Hole Logging"; Oilfield Review, Summer/Jun. 1996; pp. 28-41.

*Primary Examiner* — Marcus Taningco
(74) *Attorney, Agent, or Firm* — Cantor Colburn, LLP (57) ABSTRACT

An apparatus for estimating a property of an earth formation and a borehole fluid includes a carrier configured to be disposed in a borehole, and a pulsed neutron measurement assembly including a pulsed neutron source configured to emit neutrons into the borehole and the earth formation, and a gamma ray detector. The apparatus also includes a fluid density measurement assembly including the gamma ray detector and a gamma ray source configured to irradiate a borehole fluid with gamma rays. The gamma ray detector is positioned relative to the gamma ray source to detect both of: gamma rays resulting from neutron interactions and gamma rays emitted from the borehole fluid in response to irradiation from the gamma ray source. The apparatus further includes a processor configured to differentiate a pulsed neutron gamma ray spectrum associated with the interactions from a density gamma ray spectrum.

20 Claims, 6 Drawing Sheets

(56) References Cited

U.S. PATENT DOCUMENTS

| | | | |
|---|---|---|---|
| 5,552,598 | A | 9/1996 | Kessler et al. |
| 5,777,278 | A | 7/1998 | Bednarczyk et al. |
| 5,900,627 | A * | 5/1999 | Odom et al. .............. 250/269.7 |
| 7,253,402 | B2 | 8/2007 | Gilchrist et al. |
| 7,294,829 | B2 | 11/2007 | Gilchrist |
| 7,365,308 | B2 | 4/2008 | Trcka et al. |
| 7,446,308 | B2 | 11/2008 | Gilchrist et al. |
| 7,554,081 | B2 | 6/2009 | Riley et al. |
| 7,669,468 | B2 | 3/2010 | Wraight et al. |
| 7,755,032 | B2 | 7/2010 | Poe et al. |
| 7,804,060 | B2 | 9/2010 | Guo et al. |
| 8,039,792 | B2 | 10/2011 | Nikitin et al. |
| 8,143,570 | B2 | 3/2012 | Edwards et al. |
| 8,502,135 | B2 | 8/2013 | Chace et al. |
| 8,637,807 | B2 * | 1/2014 | Evans et al. .............. 250/269.2 |
| 2006/0192096 | A1 * | 8/2006 | Radtke et al. ............. 250/269.2 |
| 2007/0241275 | A1 | 10/2007 | Guo et al. |
| 2010/0300685 | A1 * | 12/2010 | Del Campo et al. ...... 166/254.2 |
| 2012/0166157 | A1 | 6/2012 | Whittaker |
| 2014/0330520 | A1 | 11/2014 | Kwong |
| 2014/0343857 | A1 | 11/2014 | Pfutzner et al. |
| 2015/0083905 | A1 * | 3/2015 | Jacobson et al. .......... 250/269.6 |
| 2015/0124921 | A1 * | 5/2015 | Groves et al. ................ 376/160 |
| 2015/0226875 | A1 * | 8/2015 | Climent et al. ............ 250/269.2 |

\* cited by examiner

DENSITY MEASUREMENTS USING DETECTORS ON A PULSED NEUTRON MEASUREMENT PLATFORM

BACKGROUND

Various types of logging tools are utilized by the energy industry in order to evaluate earth formations and reservoirs, for purposes such as exploration, formation evaluation, stimulation and production. Exemplary tools include resistivity tools, gamma density tools, neutron porosity tools, sonic and acoustic logging tools and pulsed neutron tools. Pulsed neutron measurement tools are utilized in downhole environments for a variety of purposes, such as neutron based formation density and porosity measurements, and neutron induced gamma-ray spectral measurements.

SUMMARY

An embodiment of an apparatus for estimating at least one property of an earth formation and a borehole fluid includes a carrier configured to be disposed in a borehole in the earth formation, and a pulsed neutron measurement assembly disposed at the carrier, the pulsed neutron measurement assembly including a pulsed neutron source configured to emit neutrons into the borehole and the earth formation, and a gamma ray detector configured to transmit signals corresponding to the detected gamma rays. The apparatus also includes a fluid density measurement assembly disposed at the carrier, the fluid density measurement assembly including the gamma ray detector and a gamma ray source configured to irradiate a borehole fluid with gamma rays. The gamma ray detector is positioned relative to the gamma ray source to detect both of: gamma rays resulting from interactions between the neutrons and at least one of the borehole and the formation, and gamma rays emitted from the borehole fluid in response to irradiation from the gamma ray source. The apparatus further includes a processor configured to receive the signals from the detector and generate gamma ray spectrum data, the processor configured to differentiate a pulsed neutron gamma ray spectrum associated with the interactions from a density gamma ray spectrum associated with the gamma rays emitted in response to the irradiation.

An embodiment of a method of estimating at least one property of an earth formation and a borehole fluid includes disposing a carrier in a borehole in the earth formation, the carrier including a pulsed neutron measurement assembly having a pulsed neutron source and a gamma ray detector, and a fluid density measurement assembly having a gamma ray source and the gamma ray detector. The method also includes emitting neutron pulses into the borehole and the earth formation from the pulsed neutron source, irradiating a borehole fluid with gamma rays from the gamma ray source, detecting by the gamma ray detector both gamma rays resulting from interactions between the neutrons and at least one of the borehole and the formation, and gamma rays emitted from the borehole fluid in response to irradiation from the gamma ray source, and receiving signals at a processor from the detector. The method further includes generating a pulsed neutron gamma ray spectrum associated with gamma rays resulting from interactions between the neutrons and at least one of the borehole and the formation, and a density gamma ray spectrum associated with gamma rays emitted in response to the irradiation, and estimating formation properties based on the pulsed neutron gamma ray spectrum, and estimating a density of the borehole fluid by estimating an attenuation of the gamma rays due to the borehole fluid based on the density gamma ray spectrum.

BRIEF DESCRIPTION OF THE DRAWINGS

The subject matter which is regarded as the invention is particularly pointed out and distinctly claimed in the claims at the conclusion of the specification. The foregoing and other features and advantages of the invention are apparent from the following detailed description taken in conjunction with the accompanying drawings in which:

DETAILED DESCRIPTION

Devices and methods are disclosed for performing formation property measurement and analysis processes. Embodiments of a formation measurement apparatus or system includes a combination pulsed neutron and fluid density measurement tool configured to take pulsed neutron measurements of a borehole and/or a formation, and take fluid density measurements in conjunction with the pulsed neutron measurements. In one embodiment, the fluid density measurements are used to estimate the holdup of one or more phases of the fluid based on the density measurements (i.e., the holdup density). The combination tool is configured to be disposed in a downhole environment, for example, in a wireline or logging-while-drilling (LWD) well logging application.

The combination tool includes a pulsed neutron measurement assembly that includes components configured to perform pulsed neutron measurements (e.g., neutron induced gamma-ray spectral measurements, formation porosity, etc.). Such components include a neutron radiation source and one or more radiation detectors configured to detect radiation generated in the borehole and the formation in response to the neutrons. In addition to components necessary or configured for the pulsed neutron measurements, a fluid density measurement assembly is incorporated into the combination tool. The fluid density measurement assembly utilizes one or more components of the pulsed neutron measurement assembly for measurement of fluid density. Fluid density measurements are useful for estimating borehole fluid properties including the holdup of phases of the fluid.

In one embodiment, the fluid density measurement assembly includes a supplemental gamma radiation source disposed proximate to or in relation to at least one radiation detector from the pulsed neutron measurement assembly (e.g., a far detector). The supplemental radiation source may be any suitable source that can emit gamma radiation independent from radiation emitted from the formation or borehole in response to pulse neutron emissions. The supplemental radiation source is configured to irradiate borehole fluid for estimating fluid properties such as fluid density. In this embodiment, the tool includes a fluid control component that positions borehole fluid between the supplemental radiation source and one of the pulsed neutron detectors. Gamma radiation from the supplemental radiation source passes through the positioned fluid and is detected by the pulsed neutron detector, and is used to estimate density of the fluid.

In one embodiment, the density measurement assembly incorporates a neutron-activated source that is configured to emit gamma radiation in response to neutrons emitted by the neutron source. The neutron-activated source is disposed proximate to the fluid control component. In one embodiment, the neutron activated source includes a material that is incorporated into one of the pulsed neutron detectors and/or is disposed at or near the pulsed neutron source. For example, the activated source includes one or more components of a sealed pulsed neutron tube. The one or more components may include a pre-existing component that is already a part of the neutron source, and/or an activated material added to a component of the neutron source (e.g., an internal or external component of a sealed neutron tube). Detection of gamma radiation from the borehole fluid in this embodiment may be accomplished using one of the pulsed neutron detectors and/or using one or more additional detectors incorporated in the tool. The neutron activated source may be located at any suitable selected location at or in the combination tool, e.g., at a location close enough to the pulsed neutron source to excite or cause gamma radiation that can be used to irradiate borehole fluid and perform density or other fluid property measurements.

Any suitable gamma radiation source may be incorporated with the combination tool, and is not limited to those described herein. For example, some detectors such as gamma ray scintillators can have their own internal radioactivity, e.g., scintillator-generated radiation due to internal decays. Borehole fluid can be drawn or positioned relative to one or more detectors so that the fluid (or fluid sample) is irradiated by the detector's internal radiation.

The combination tool takes advantage of pre-existing pulsed neutron tool configurations and provides an apparatus or system that can be used simultaneously or concurrently for both pulsed neutron and density measurements. The systems and methods described herein provide numerous advantages, such as increased efficiency due to the ability to employ multiple measurement regimes in a single tool, and reduced cost and manufacturing complexity.

Figure 1:
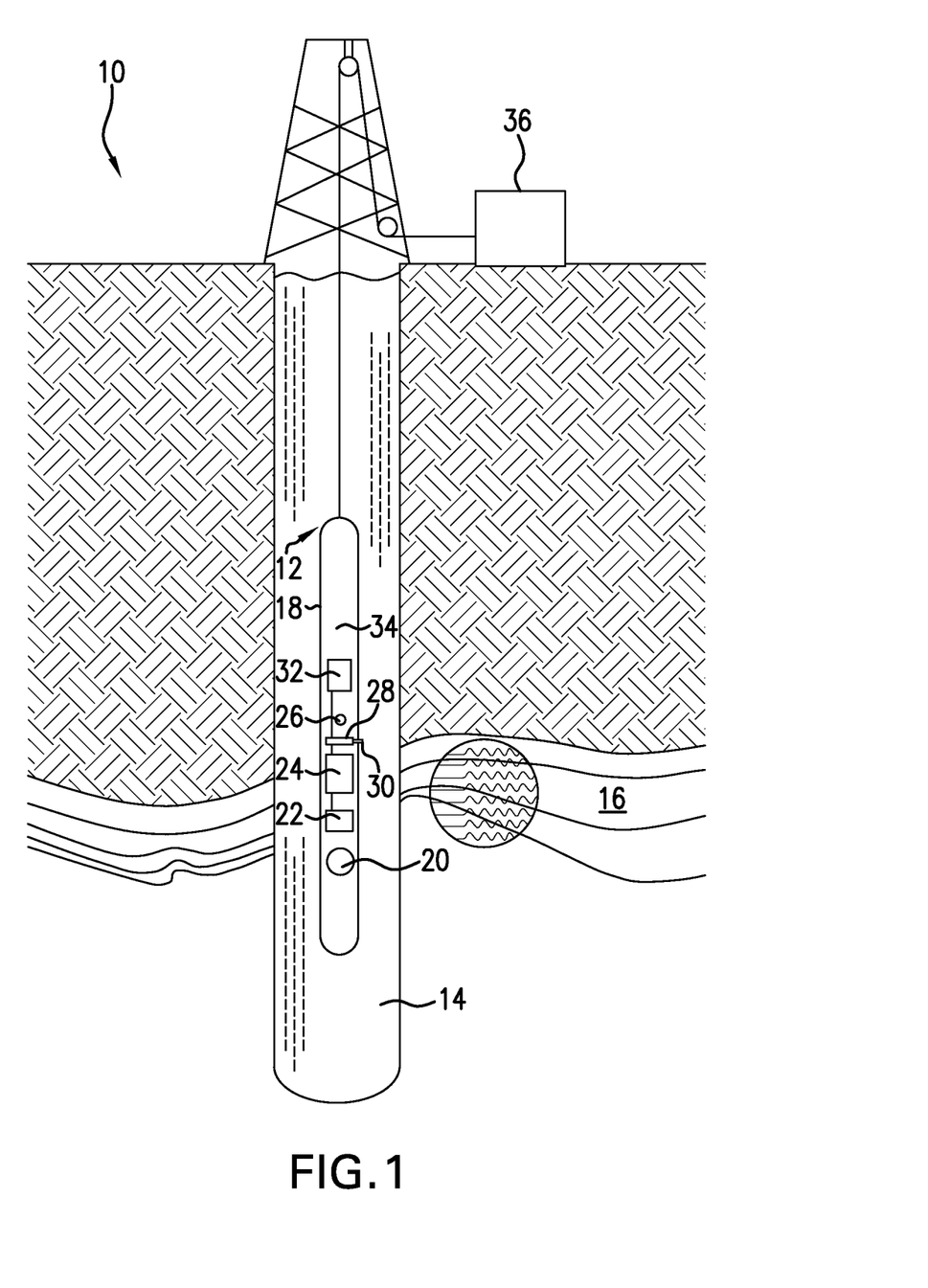
FIG. 1 is a side cross-sectional view of an embodiment of a subterranean well drilling, evaluation, exploration and/or production system.

Referring to FIG. 1, an exemplary embodiment of a subterranean well drilling, evaluation, exploration and/or production system 10 includes a borehole string 12 that is shown disposed in a borehole 14 that penetrates at least one earth formation 16 during a subterranean operation. As described herein, "formations" refer to the various features and materials that may be encountered in a subsurface environment and surround the borehole. The borehole 14 is a cased borehole or an open borehole, or has both cased and open portions. In one embodiment, the borehole string includes a downhole tool 18 such as a well logging tool. In this example, the downhole tool 18 is a wireline tool, but is not limited thereto. For example, the downhole tool 18 can be incorporated with a drill string for logging-while-drilling (LWD) applications. The downhole tool 18 is not limited to the embodiments described herein, and may be disposed with any suitable carrier. A "carrier" as described herein means any device, device component, combination of devices, media and/or member that may be used to convey, house, support or otherwise facilitate the use of another device, device component, combination of devices, media and/or member. Exemplary non-limiting carriers include drill strings of the coiled tube type, of the jointed pipe type and any combination or portion thereof. Other carrier examples include casing pipes, wirelines, wireline sondes, slickline sondes, drop shots, downhole subs, bottom-hole assemblies, and drill strings.

The downhole tool 18 is configured as a combination pulsed neutron and density measurement tool, which includes a pulsed neutron measurement assembly and a density measurement assembly. The pulsed neutron measurement assembly includes, for example, at least one pulsed neutron source 20 (e.g., a sealed neutron tube) and one or more radiation detectors, such as gamma ray detectors and neutron detectors. An exemplary detector is a scintillation detector that is capable of generating signals and/or data representative of inelastic and/or capture gamma ray energy spectra. In one embodiment, the tool 18 includes a plurality of detectors, such as a near detector 22 positioned at a first location, and a far detector 24 positioned at a second location that is further from the neutron source 20 than the first position. The near and far detectors are shown as axially aligned with the neutron source 20 (i.e., along a longitudinal axis of the tool and/or the borehole), although the tool 18 may have other configurations.

Pulsed neutron measurements are based on bursting neutrons into a formation zone around the borehole and consequently monitoring of neutron counts and decay due to scattering and capturing effects. Pulsed neutron measurements include measurements such as carbon/oxygen ratio (C/O) and Sigma measurements, which are useful in estimating reservoir oil saturation, and lithology estimations from elemental yields based on analysis of inelastic and capture gamma ray spectra.

One embodiment of the density measurement assembly includes a gamma ray ("γ") source 26 configured to irradiate or illuminate borehole fluid with gamma ray photons. As described herein, "borehole fluid" includes any flowable material that is advanced through the borehole, including liquids, gases and flowable solids. The borehole fluid may include fluids produced from the formation, such as oil, natural gases, non-hydrocarbon gases, sand, cuttings and water. Other examples of borehole fluid include drilling fluid, injection fluid, stimulation fluids and other materials injected into the borehole. In one embodiment, the borehole fluid is a single or multi-phase fluid having constituents that include concentrations of phases such as liquid hydrocarbons (e.g., oil), gases and/or water.

For density measurements, both the gamma ray source 20 and the far detector 24 are positioned proximate to the fluid, and a beam of gamma rays is emitted from the gamma ray source (e.g., a Caesium-137 source, etc.). The gamma ray source may be any suitable radioactive isotopes or radioactive material that emit gamma rays having a dynamic range sufficient for fluid measurements. Sources may be selected that have desired energy levels that cause emissions from fluid that can be measured to estimate fluid properties. Such energy levels can be selected based on considerations such as the type and volume of material to be irradiated.

Gamma rays pass through the fluid and/or are scattered by the fluid are detected by the far detector 24. The incident photons are absorbed and/or scattered (sometimes scattered and then absorbed) by the fluid resulting in lower number of photons reaching the detector. The attenuation of the gamma rays by the fluid is used to estimate the density.

In one embodiment, the tool 18 includes a fluid control component 28 or other feature configured to take a sample of borehole fluid or allow borehole fluid to flow into or through the tool 18. For example, as shown in FIG. 1, the tool 18 includes a sample chamber or flow-through conduit coupled to a port 30 configured to draw borehole fluid into the sample chamber 28. The port includes sufficient components such as valve devices and/or outlet port to allow for control of the fluid sample.

The gamma ray source 26 is positioned proximate the fluid control device, i.e., close enough to the fluid control device so that a sufficient amount of gamma radiation is incident on the borehole fluid to allow for effective measurement of scattering or attenuation of the radiation. In addition, the fluid control device and the gamma ray source 26 are positioned relative to the far detector 24 so that the far detector 24 can detect gamma rays from the borehole fluid and be used for density measurements.

The downhole tool 18 includes a housing 34 such as a sonde configured to house components of the pulsed neutron measurement assembly and the fluid density measurement assembly. The housing 34 forms part of a wireline logging tool in the embodiment of FIG. 1, but is not so limited. For example, the tool 18 may incorporated as or in a LWD tool, production string or injection string as desired.

The system 10 also includes one or more surface and/or downhole processors or processing devices. For example, downhole electronics 32 are incorporated in the tool 18 or in communication with the tool 18, and are configured to perform control, data collection, data transmission and/or analysis functions. In one embodiment, the tool 18 is equipped with transmission equipment to communicate ultimately to a surface processing unit 36. Such transmission equipment may take any desired form, and different transmission media and methods may be used. Examples of connections include wired, fiber optic, and wireless connections. The electronics 32 and/or the surface processing unit 36 perform various functions, such as control of the downhole components (e.g., the neutron and gamma ray sources, the detectors, and the fluid control device), collecting and transmitting detector signals and data, and/or processing data for estimating formation and borehole fluid properties.

Various types of gamma radiation sources and configurations of the tool 18 are shown in FIGS. 2-5. The tool 18 can have a variety of configurations and include different types of gamma ray sources, and is not limited to the embodiments described herein.

In these embodiments, the tool includes a plurality of detectors, such as a short space (SS) detector 40, a long space (LS) detector 42 and/or an extra-long space (XLS) detector 44. The SS detector 40 is positioned at a first distance from the neutron source 20, and the XLS detector 44 is positioned at a second distance from the neutron source 20 that is greater than the first distance. In some embodiments, at least one additional detector, referred to as the LS detector 42, is positioned between the SS and the XLS detectors.

Also in these embodiments, the fluid control component includes a flow-through chamber 46 having an inlet 48 and an outlet 50. A valve or other flow control device may be disposed at or near the inlet 48 and/or the outlet 50 to allow the flow of fluid through the chamber 46 to be controlled. For example, the valve(s) can be open or closed to control when fluid is allowed to flow through the chamber (e.g., for sampling), or partially open or closed to regulate the pressure and/or flow rate of fluid within the chamber. Fluid may be allowed to flow continuously through the fluid chamber 46 as measurements are performed, or held within the chamber 46 during a gamma ray and/or pulsed neutron measurement time window and then released.

Figure 2:
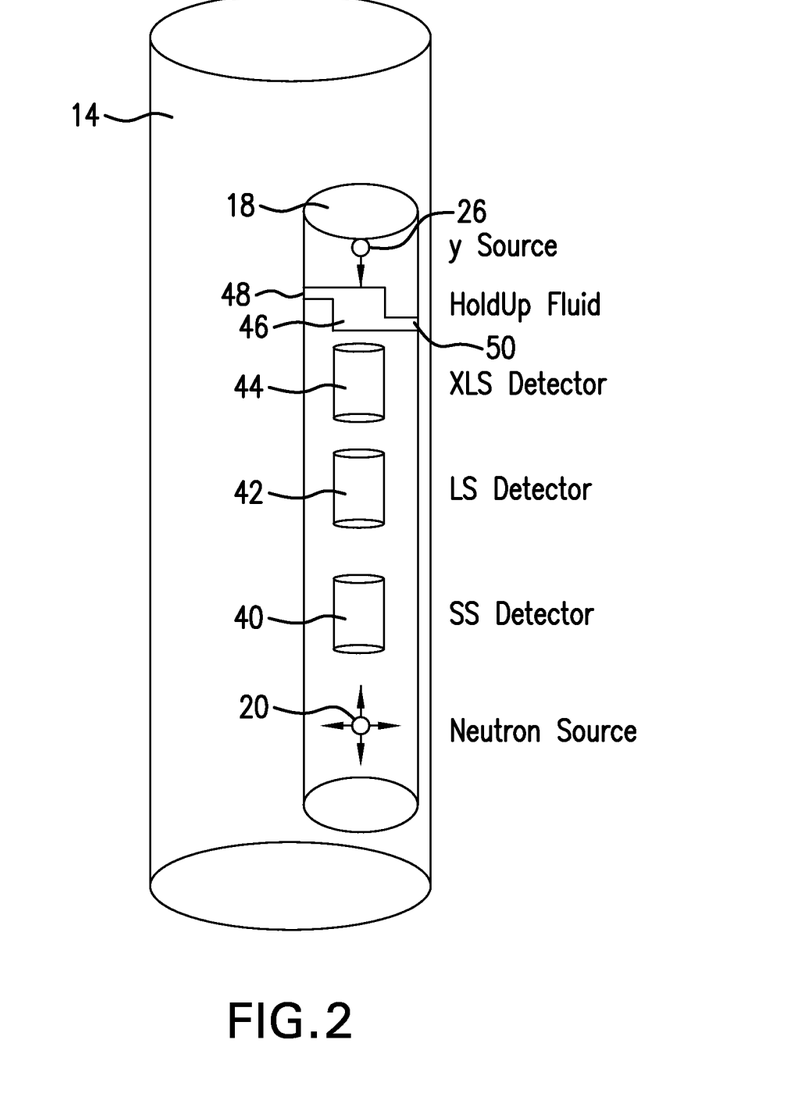
FIG. 2 depicts an embodiment of a combination pulsed neutron and fluid density measurement tool.

Referring to FIG. 2, in one embodiment, the gamma ray source 26 is a chemical source that is placed near the chamber 46 and on an opposite side of the chamber relative to the XLS detector 44. The gamma rays from the source 26 are used to illuminate the fluids in the chamber 46, and gamma rays transmitted through the fluid are counted in the XLS detector 44 (or other detector) to produce a gamma ray spectrum (also referred to as a density gamma ray spectrum) that can be analyzed to determine attenuation of the gamma rays and a corresponding density.

As shown in FIG. 2, in one embodiment the tool 18 is configured so that gamma radiation transmitted through the fluid is detected by a far detector, e.g., the LS or XLS detector. One benefit of this embodiment is that the far detector typically experiences a much lower count rate than the near detector from a pulsed neutron generator, which allows for easier differentiation between gamma ray spectra associated with density and spectra associated with pulsed neutron interactions.

Figure 3:
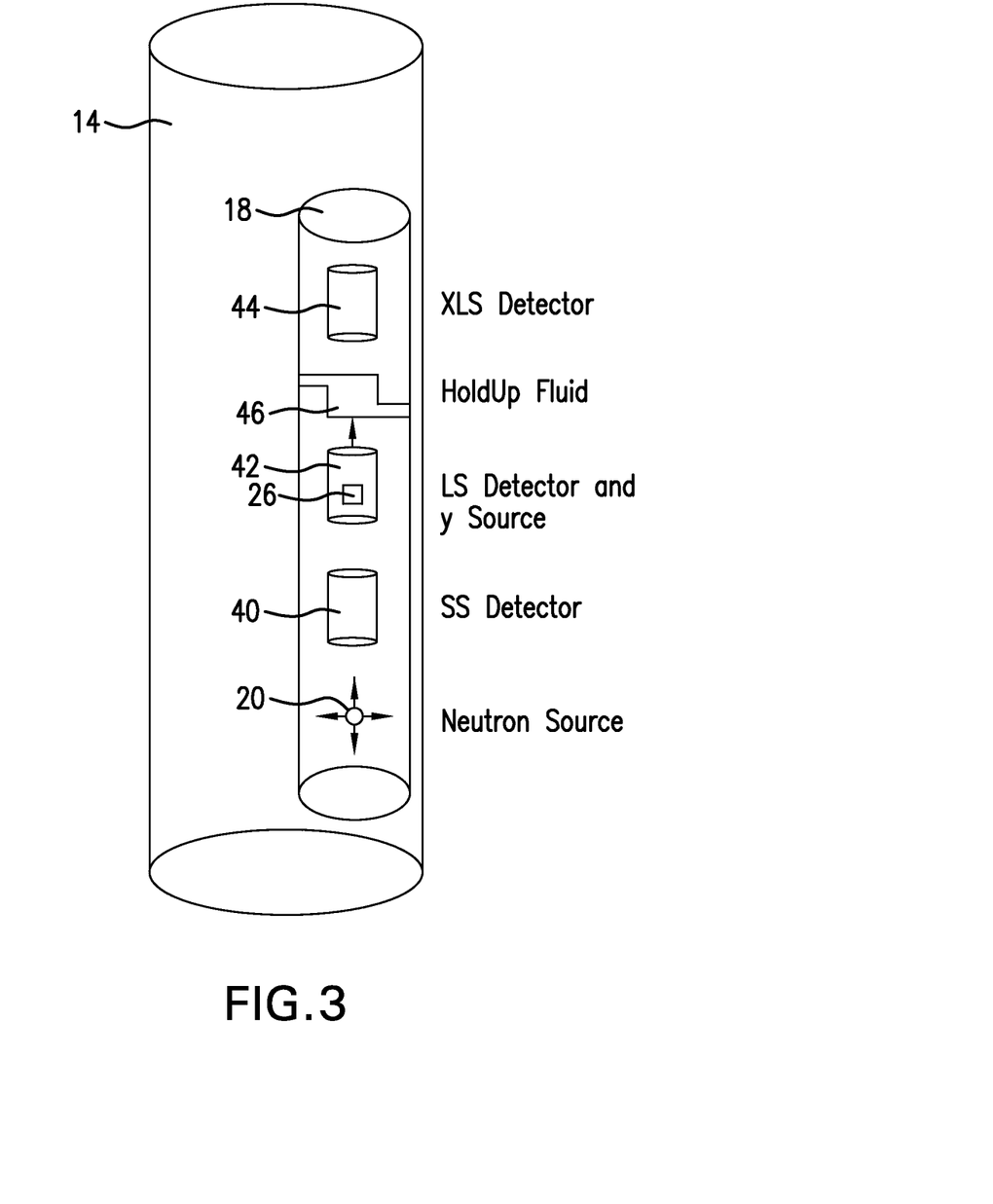
FIG. 3 depicts another embodiment of a combination pulsed neutron and fluid density measurement tool.

Referring to FIG. 3, in one embodiment, the gamma ray source 26 includes a source material that functions as both a gamma ray or neutron detector as well as a gamma ray source. For example, the LS detector 42 includes a scintillator crystal that has its own naturally occurring gamma ray emission that is produced independent of the neutron-induced gamma radiation, i.e., has self-radioactivity. With this configuration, the detector 42 can be used as a detector in normal pulsed neutron logging and can also be used as a source that will illuminate the borehole fluid.

Examples of scintillators having self-radioactivity include those that include Lanthanum (La), such as LaBr3:Ce and LaCl3:Ce, and Lutetium (Lu) based scintillators such as LuxY2-x(SiO4)O:Ce (LYSO), LuAlO3:Ce (LuAP:Ce), Lu3Al5O12:Ce (LuAG:Ce), Lu3Al5O12:Pr (LuAG:Pr) and others. Such materials may be incorporated into the detector as scintillator crystals. The naturally-occurring radiation emitted by the crystal can be differentiated from gamma rays emitted from the formation by filtering or otherwise processing the measured data using energy thresholds.

Figure 4:
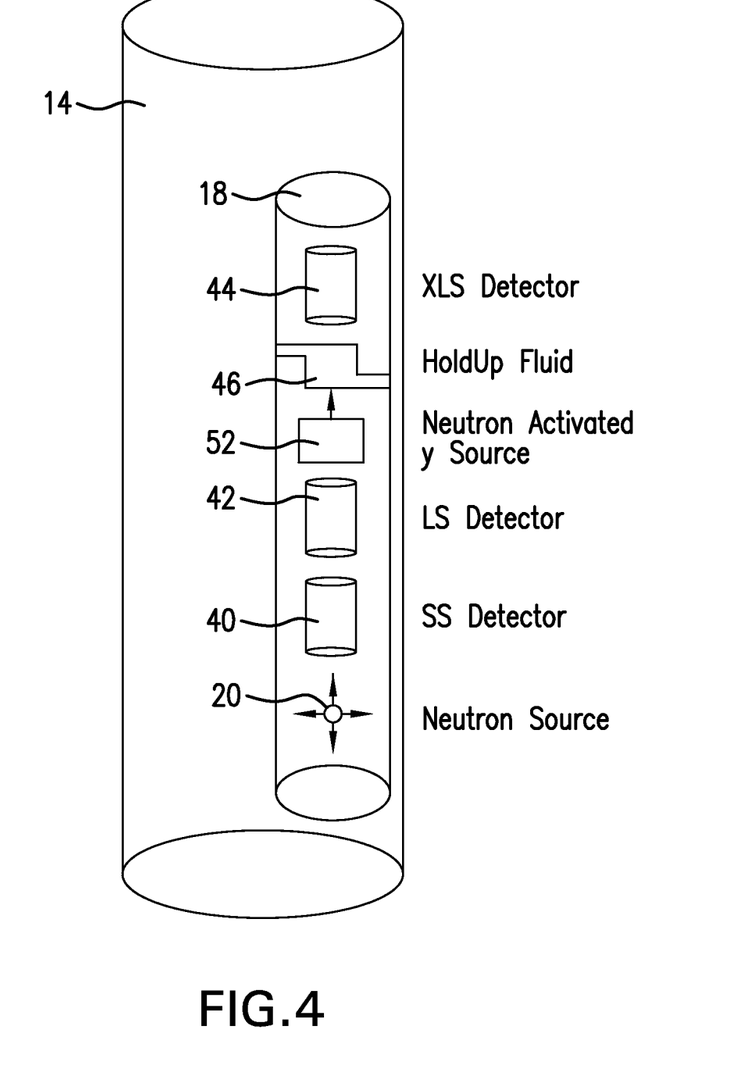
FIG. 4 depicts a further embodiment of a combination pulsed neutron and fluid density measurement tool.
Figure 5:
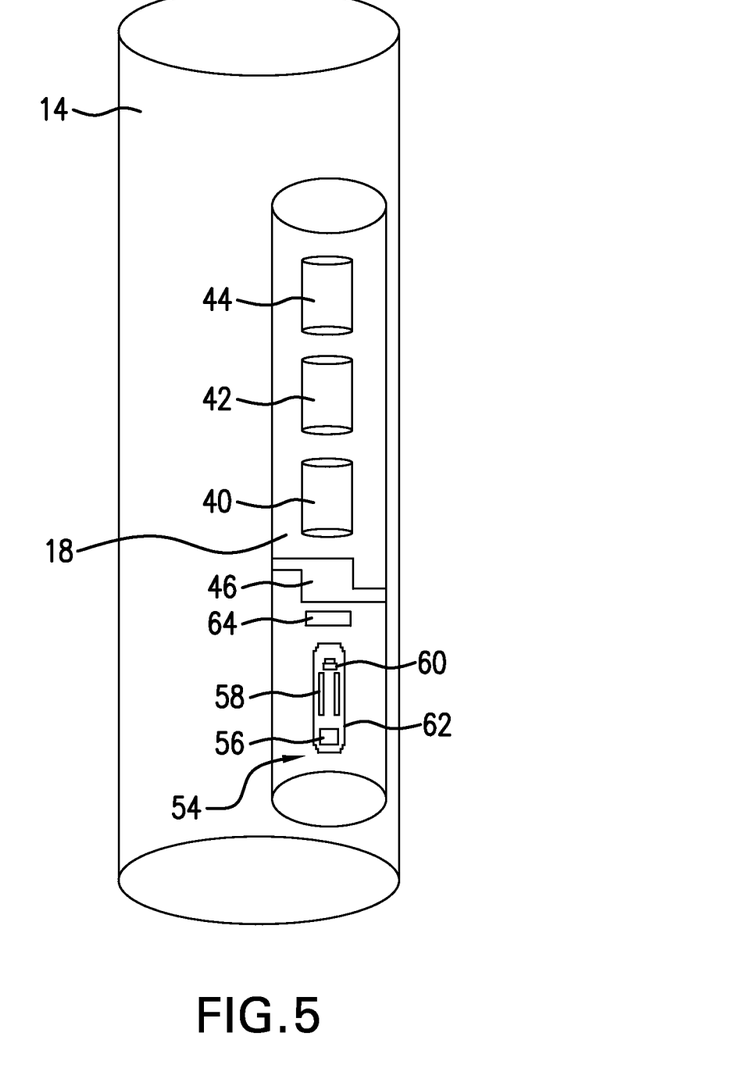
FIG. 5 depicts yet another embodiment of a combination pulsed neutron and fluid density measurement tool.

FIGS. 4 and 5 show embodiments in which the gamma ray source is a neutron-activated source. A neutron-activated source includes a material that emits gamma radiation due to neutrons impinging on the material. In these embodiments, the gamma ray source is activated by neutrons emitted from the neutron source 20 through activation reactions. Referring to FIG. 4, one embodiment includes a neutron-activated source 52 disposed on one side of the fluid control device 46. In response to neutron bursts emitted from the neutron source 20, the neutron-activated source emits gamma rays into the borehole fluid, and gamma rays scattered in and transmitted through the borehole fluid are detected by the XLS detector 44.

FIG. 5 shows another embodiment that utilizes neutron-activated gamma ray sources. In this embodiment, the neutron source 20 is configured as a sealed neutron tube 54 that includes components for accelerating ions and emitting neutrons in response to the application of appropriate energy, e.g., electric signals from a downhole or surface power source. The neutron tube 54 acts as a neutron emitter or source and interacts with the neutron-activated source.

The neutron tube 54 includes an ion source 56, an accelerating electrode 58 and a target 60. Ions such as Deuterium ions are discharged from the ion source 56 and collide with the target 60, thereby generating neutrons. For example, the target is a Tritium target and neutrons are generated as a result of Deuterium-Tritium (D-T) fusion reactions. The components of the neutron tube are disposed in a housing 62, such as a vacuum tight enclosure. In one embodiment, the neutron tube 54 is a cylindrical tube, although any suitable shape or configuration may be used.

One or more neutron-activated source materials are disposed at or near the neutron tube 54, which can be separate components, form components of the neutron tube 54 or be additional components added to the neutron tube 54. The activation products of the tube 54, either as a sum of contributions or as materials with specific energies and decay characteristics, are used as the source of gamma ray photons for conducting fluid density measurements with either flowing or sampled borehole fluids.

In one embodiment, the neutron-activated source material is formed as the substrate of the Tritium target 60. The target 60 includes a disc shaped or cylindrical substrate made from a metal such as silver or copper, and a hydrogen occluding material (e.g., titanium) deposited on the substrate and suitable for producing the D-T fusion reaction. The substrate in this embodiment is made from a material that emits gamma rays in response to interaction with the neutrons generated at the target 60.

For a planar substrate and an approximate point source beam for neutron production, approximately half of the fast neutrons generated by the target 60 traverse some segment of the substrate material. Fast neutron activation of that substrate material can be used as the source of gamma rays to conduct the density measurement with either existing gamma ray detectors (e.g., the SS detector 40) or with the addition of another gamma ray detector proximate to the flowing or sampled borehole fluid in the fluid control device 46 and the sealed neutron tube 54.

The tool 18 includes the fluid control device 46 positioned so that gamma rays emitted from the neutron-activated material irradiate the borehole fluid. The gamma rays for density measurement can be differentiated from pulse neutron measurements by selecting time windows during which no significant neutron generation is occurring, e.g., during an extended background gate after the time windows (or time gates) used for inelastic and thermal capture spectra.

In one embodiment, an additional gamma ray detector 64 is placed between the neutron tube 54 and the fluid chamber 46 to monitor variations in the gamma ray source strength. This embodiment allows the applied gamma ray intensity to be normalized so that density measurements can be taken as the neutron tube 54 emits varying gamma ray intensities and/or energies. Here, a fast neutron detector can be placed as well to normalize the yield from the neutron generator. This can have advantages in that the fast neutron detector counts will not depend from the surrounding formation, while counts from the gamma detector may depend both from neutron generator output and the surrounding formation.

In some instances, the neutron tube 54 includes multiple components that have natural or neutron-activated components. In such instances, energy windows are selected for analyzing detector counts that correspond to gamma ray energies emitted by the different components. For example, an energy window or windows is selected for gating an appropriate energy associated with a specific target substrate material or other component, such as the relatively long lived channel for Cu-65 which has an activation product reaction represented as 65Cu(n,p)65Ni, with a beta decay reaction energy of 1.352 MeV, and is sufficiently naturally isotopically abundant (30.8) with a good activation cross section of 1100 barns. An energy window corresponding to the gamma ray energies emitted by this component is selected. As discussed above, a detector such as the detector 64 may be positioned so that the initial intensity or counts for gamma rays in the energy window are determined and can be compared with counts emitted from the borehole fluid.

Other candidate substrates include, for example Molybdenum, iron, nickel and other elements or isotopes. Substrates or other component materials may be selected based on, e.g., half-life and energy levels of emitted gamma rays.

Figure 6:
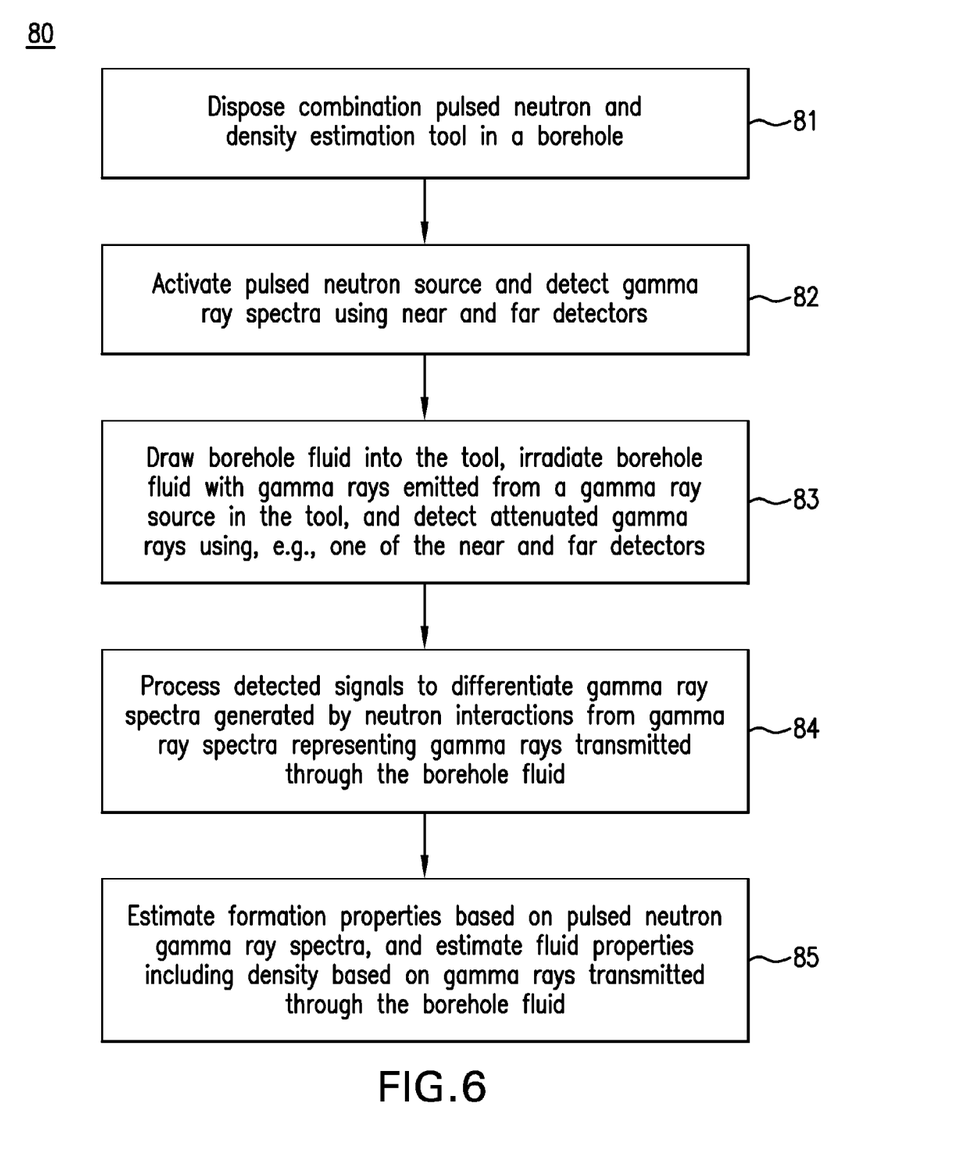
FIG. 6 is a flowchart depicting an embodiment of a method of estimating properties of a formation and borehole fluid.

FIG. 6 shows an embodiment of a method 80 of estimating properties of an earth formation and borehole fluids. The method 80 may be performed by a processor such as the surface processing unit 36 and/or the electronics 32, but is not so limited. Any suitable processor or processing device capable of receiving measurement data from the tool may be used. The method 80 is discussed below in conjunction with the system 10 for illustrative purposes, but may be used with any suitable configuration, such as those shown in FIGS. 2-5. The method 80 includes one or more stages 81-85. In one embodiment, the method 80 includes the execution of all of stages 81-85 in the order described. However, certain stages may be omitted, stages may be added, or the order of the stages changed.

In the first stage 81, the tool 18 is disposed in the borehole 14. The tool 18 may be disposed and activated for measurement in a running well or a well that has been shut in. In one embodiment, the tool 18 is a wireline tool but may be used in other contexts, such as LWD applications. Measurements and analysis may be performed at multiple times and depths to produce gamma ray spectrum data such as C/O logs and density logs.

In the second stage 82, the pulsed neutron source 20 is activated to emit a series of bursts over a selected time window. The processing unit and/or electronics produce pulses by turning the neutron source on and off during a time window. For example, an electronic timing gate synchronizes timing of the neutron pulses with detection by the detectors. "Synchronizing" relates to initiating the neutron pulse PNG and recording the start time when the neutron source is "on" (i.e., beginning of pulse), the time when the neutron source is "off" (i.e., end of pulse), the time proceeding after the pulse emission ends, and neutron detection times as they relate to the on and off times.

The near and far detectors 22 and 24 detect gamma rays at selected time gates, i.e., selected time periods within the time window or subsets of the time window. Among these time gates are an inelastic time gate corresponding to the time of detection of gamma rays emitted due to inelastic scattering, which occurs during the neutron burst when the neutrons have relatively high energy levels to be able to induce inelastic scattering gamma ray emissions. The inelastic scattering generates gamma rays (inelastic gamma rays) that can be detected by the detectors as inelastic spectra. In some instances, gamma rays are measured during the inelastic time gate come not only from inelastic interactions but also from thermal capture interactions as well, and thus the detected count rate is a total (inelastic and thermal capture) count rate. Another step may be performed to remove the thermal capture gamma counts to obtain the inelastic gamma rays.

The detectors also detect gamma rays during thermal time gates corresponding to thermal interactions, in which neutrons having thermal energies are captured or absorbed by the nuclei of elements in the formation. At thermal energies, neutrons continue to undergo elastic collisions, but they no longer lose energy on average.

In the third stage 83, the fluid density measurement assembly is used to irradiate borehole fluid and detect gamma rays emitted from the borehole fluid in response to the irradiation.

In one embodiment, borehole fluid is drawn into a fluid control component such as the fluid chamber 46. The borehole fluid may be allowed to continuously or periodically flow through the fluid chamber 46 during measurements, or drawn in and held as a fluid sample, which can be released back into the borehole after the measurement is performed.

Gamma rays are emitted from the gamma ray source 20, such as a chemical source or a source activated by neutrons, e.g., components of the sealed neutron tube 54 and/or the neutron activated source 52. Gamma rays that are transmitted and scattered through the fluid are detected by, e.g., the far detector 24, the LS detector 42 and/or the XLS detector 44. The gamma ray source may be a separate source (e.g., a chemical source or neutron-activated source) or part of a pre-existing pulsed neutron assembly component (e.g., neutron-activated components of the pulsed neutron generator or internal radioactivity of a detector).

In one embodiment, the density measurement is performed by irradiating the fluid with gamma rays having different energy levels than gamma rays expected to be detected during the pulsed neutron measurements, and/or by counting only those gamma rays that have energies at or around the principal energy of the gamma rays used to irradiate the borehole fluid. This embodiment allows the density gamma ray spectra to be differentiated from the pulsed neutron spectra by, e.g., gating or binning the detected gamma ray spectra by energy.

Gamma rays may be applied to the borehole fluid and/or detected at selected time windows or gates that allow for the density gamma ray spectra to be differentiated. In one embodiment, gamma rays are detected during selected time windows or gates that are different than the inelastic time gates and the thermal time gates, or the detector 22 is configured to count gamma rays only during the selected time gates. For example, gamma rays are emitted and/or detected during the background time gate of a pulsed neutron measurement cycle, which occurs after the inelastic and thermal time gates. In another example, an extended background gate is selected for detecting gamma rays from the borehole fluid (which is longer than the background time gate selected for pulsed neutron measurement). This allows for more effective differentiation, as there are typically no or relatively few gamma rays resulting from the neutron interactions.

In the fourth stage 84, signals and data generated by the pulsed neutron and/or density measurement assemblies are processed to differentiate gamma ray spectra resulting from neutron interactions (pulsed neutron gamma ray spectra) from gamma ray spectra resulting from gamma rays transmitted through or scattered by the borehole fluid (density gamma ray spectra). For example, gamma ray signals detected during a pulsed neutron measurement cycle are divided or separated into different time gates corresponding to the inelastic, thermal and background time gates. The spectra in the inelastic and thermal time gates are processed to generate pulsed neutron spectra, and the spectra in the background or extended background gates are processed to generate fluid density spectra. This processing may include gating data by energy level as discussed above.

In the fifth stage 85, formation and/or borehole fluid properties are estimated using the processed gamma ray spectra.

Various properties or information indicative of formation properties may be estimated from the pulsed neutron gamma ray spectra, such as porosity, saturation, sigma values, minerology and carbon-oxygen (C/O) ratios. Inelastic spectrum data and the capture spectrum data are processed to determine the elemental weight fractions (i.e., elemental concentrations expressed as a percent of mass of the sample) of multiple elements. Time spectra from near and far detectors can be processed individually to provide traditional thermal neutron capture cross section sigma information, or the two spectra can be used together to automatically correct for borehole and diffusion effects and produce results substantially approximating intrinsic formation sigma values.

An exemplary measurement is a C/O measurement, which is performed by the tool 18 and generates results such as a C/O log. C/O ratios are estimated based on spectral analysis of the inelastic gamma ray spectra to estimate the amounts of oxygen and carbon in the volume of investigation, which can be used in conjunction with lithology and other information to obtain an estimate of oil and water concentration in the formation.

The density gamma ray spectra are analyzed to estimate density or other properties of the borehole fluid. The energy and intensity of gamma rays used to irradiate the fluid is known based on the source used, or may be measured by a gamma ray detector disposed between the gamma ray source and the borehole fluid, e.g., the detector 64. The density gamma ray spectra are compared to the applied spectra to estimate attenuation of the gamma rays, which is then used to estimate density.

In one embodiment, holdup density properties of the fluid are estimated. The holdup of a particular phase of the borehole fluid (e.g., the gas, oil and/or water phase holdup) refers to the fraction of the cross-sectional area of the casing or borehole that is occupied by the phase. The density measurements performed at one or more depths or locations along the borehole using the density measurement assembly are analyzed to estimate the holdup of different phases in the borehole fluid.

In one embodiment, the pulsed neutron and gamma ray measurements are performed in a running well during production. For example, as fluid flows toward the surface, a portion is drawn through the fluid chamber in the tool and is irradiated. This may be performed simultaneously with neutron irradiation or at a separate time.

Although embodiments shown draw fluid within the tool, they are not so limited. For example, the tool 18 may be configured without a fluid chamber and the gamma ray beam from the gamma ray source 26 is emitted toward the annulus or inward to a central tool bore. A shield (e.g., a tungsten disc) may be disposed between the gamma ray source 26 and the far detector. Backscattered radiation from the fluid is then detected by a gamma ray detector such as the far detector 24, and the resulting gamma ray spectra are processed and analyzed as discussed above.

The apparatuses and methods described herein have various advantages over prior art apparatuses and techniques. The apparatuses and methods allow for the simultaneous or concurrent measurement of formation properties using pulsed neutron techniques and fluid properties using gamma ray density techniques. In addition, manufacturing and logging operations can be made more cost-effective and simpler by incorporating these measurements in a single tool that uses common components (e.g., detectors and/or neutron sources) to perform these techniques.

For example, embodiments described herein allow for measurement of holdup density during a pulsed neutron and/or C/O log, so that the pulsed neutron and/or C/O logs can be performed during running conditions. This is in contrast to typical C/O logging runs, which are performed during shut-in conditions.

Furthermore, embodiments described herein can be used to take advantage of gamma radiation that is already produced by pulsed neutron tool components. For example, electrically driven, sealed neutron tube device for well logging applications are used by the oilfield industry. A detrimental side effect of the use of these devices has been the presence of unwanted gamma rays produced by the interaction of neutrons with materials of the devices. These interactions occur in the same way that the neutrons interact in interrogating borehole and formation constituents. That is, there are inelastic, capture, and activation events that occur within the materials of construction of the emitting device itself that do not normally lend themselves to any desirable formation evaluation capability.

To the contrary, such events are usually considered a contaminating or parasitic component to be handled appropriately. Embodiments described herein can utilize these previously unwanted events to provide a fluid holdup density measurement.

In connection with the teachings herein, various analyses and/or analytical components may be used, including digital and/or analog systems. The system may have components such as a processor, storage media, memory, input, output, communications link (wired, wireless, pulsed mud, optical or other), user interfaces, software programs, signal processors (digital or analog) and other such components (such as resistors, capacitors, inductors and others) to provide for operation and analyses of the apparatus and methods disclosed herein in any of several manners well-appreciated in the art. It is considered that these teachings may be, but need not be, implemented in conjunction with a set of computer executable instructions stored on a computer readable medium, including memory (ROMs, RAMs), optical (CD-ROMs), or magnetic (disks, hard drives), or any other type that when executed causes a computer to implement the method of the present invention. These instructions may provide for equipment operation, control, data collection and analysis and other functions deemed relevant by a system designer, owner, user or other such personnel, in addition to the functions described in this disclosure.

One skilled in the art will recognize that the various components or technologies may provide certain necessary or beneficial functionality or features. Accordingly, these functions and features as may be needed in support of the appended claims and variations thereof, are recognized as being inherently included as a part of the teachings herein and a part of the invention disclosed.

While the invention has been described with reference to exemplary embodiments, it will be understood by those skilled in the art that various changes may be made and equivalents may be substituted for elements thereof without departing from the scope of the invention. In addition, many modifications will be appreciated by those skilled in the art to adapt a particular instrument, situation or material to the teachings of the invention without departing from the essential scope thereof. Therefore, it is intended that the invention not be limited to the particular embodiment disclosed as the best mode contemplated for carrying out this invention.

The invention claimed is:

1. An apparatus for estimating at least one property of an earth formation and a borehole fluid, comprising:
   a carrier configured to be disposed in a borehole in the earth formation;
   a pulsed neutron measurement assembly disposed at the carrier, the pulsed neutron measurement assembly including a pulsed neutron source configured to emit neutrons into the borehole and the earth formation, and a gamma ray detector configured to detect gamma ray signals during a pulsed neutron measurement cycle;
   a fluid density measurement assembly disposed at the carrier, the fluid density measurement assembly including the gamma ray detector and a gamma ray source configured to irradiate a borehole fluid with gamma rays, wherein the gamma ray detector is positioned relative to the gamma ray source to detect gamma ray signals including both of: pulsed neutron gamma ray signals including gamma rays resulting from interactions between the neutrons and at least one of the borehole and the formation, and gamma density signals including gamma rays that pass through the borehole fluid in response to irradiation from the gamma ray source, the gamma ray detector configured to detect the gamma ray signals during a plurality of different selected time gates within the pulsed neutron measurement cycle, the plurality of selected time gates including one or more first time gates associated with the pulsed neutron gamma ray signals and one or more second time gates associated with the gamma density signals; and
   a processor configured to receive the gamma ray signals from the detector and generate gamma ray spectrum data, the processor configured to differentiate a pulsed neutron gamma ray spectrum associated with the pulsed neutron gamma ray signals from a density gamma ray spectrum associated with the gamma density signals based on a time during the pulsed neutron measurement cycle at which gamma rays were detected.

2. The apparatus of claim 1, wherein the pulsed neutron measurement assembly includes a first detector and a second detector located further from the neutron source than the first detector, and the gamma ray detector is configured as the second detector.

3. The apparatus of claim 1, further comprising a fluid control component configured to draw fluid into the apparatus, the fluid control component including a fluid chamber located proximate to the gamma ray detector and the gamma ray source and positioned between the gamma ray detector and the gamma ray source.

4. The apparatus of claim 2, wherein the gamma ray source is disposed within the first detector.

5. The apparatus of claim 4, wherein the first detector is a scintillation detector and the gamma ray source is a scintillation material having a natural gamma ray emission.

6. The apparatus of claim 1, wherein the gamma ray source includes a neutron-activated material, the neutron-activated material configured to emit gamma rays toward the borehole fluid in response to neutrons from the neutron source impinging on the neutron-activated material.

7. The apparatus of claim 6, wherein the neutron source is a sealed neutron tube, and the neutron-activated material includes one or more components of the sealed neutron tube.

8. The apparatus of claim 7, wherein the neutron source includes an ion source and a target configured to emit neutrons in response to ions, and the neutron-activated material is a component of the target.

9. The apparatus of claim 1, wherein the processor is configured to estimate formation properties based on the pulsed neutron gamma ray spectrum, and is configured to estimate a density of the borehole fluid by estimating an attenuation of the gamma rays due to the borehole fluid based on the density gamma ray spectrum.

10. The apparatus of claim 3, wherein the carrier includes a protective housing surrounding the pulsed neutron source, the gamma ray detector, the gamma ray source and the fluid chamber.

11. A method of estimating at least one property of an earth formation and a borehole fluid, comprising:
disposing a carrier in a borehole in the earth formation, the carrier including a pulsed neutron measurement assembly having a pulsed neutron source and a gamma ray detector, and a fluid density measurement assembly having a gamma ray source and the gamma ray detector;
emitting neutron pulses into the borehole and the earth formation from the pulsed neutron source during a pulsed neutron measurement cycle;
irradiating a borehole fluid with gamma rays from the gamma ray source during the pulsed neutron measurement cycle;
detecting by the gamma ray detector gamma ray signals during the pulsed neutron measurement cycle, the gamma ray signals including both pulsed neutron gamma ray signals including gamma rays resulting from interactions between the neutrons and at least one of the borehole and the formation, and gamma density signals including gamma rays emitted from the borehole fluid in response to irradiation from the gamma ray source, the gamma ray detector detecting the gamma ray signals during a plurality of different selected time gates within the pulsed neutron measurement cycle, the plurality of selected time gates including one or more first time sates associated with the puked neutron gamma ray signals and one or more second time gates associated with the gamma density signals; and
receiving the gamma ray signals at a processor from the detector, and performing:
generating a pulsed neutron gamma ray spectrum associated with the pulsed neutron gamma ray signals based on gamma rays detected during the one or more first time gates, and generating a density gamma ray spectrum associated with the gamma density signals based on gamma rays detected during the one or more second time gates; and
estimating formation properties based on the pulsed neutron gamma ray spectrum, and estimating a density of the borehole fluid by estimating an attenuation of the gamma rays due to the borehole fluid based on the density gamma ray spectrum.

12. The method of claim 11, wherein the pulsed neutron measurement assembly includes a first detector and a second detector located further from the neutron source than the near detector, and the gamma ray detector is configured as the second detector.

13. The method of claim 11, wherein irradiating the borehole fluid includes drawing fluid into a fluid chamber located proximate to the gamma ray detector and the gamma ray source and positioned between the gamma ray detector and the gamma ray source.

14. The method of claim 12, wherein the gamma ray source is disposed within the first detector.

15. The method of claim 14, wherein the first detector is a scintillation detector and the gamma ray source is a scintillation material having a natural gamma ray emission, and irradiating the borehole fluid includes disposing the borehole fluid proximate to the first detector so that the natural gamma ray emission impinges on the borehole fluid.

16. The method of claim 11, wherein the gamma ray source includes a neutron-activated material, and irradiating the borehole fluid includes emitting gamma rays toward the borehole fluid from the neutron-activated material in response to neutrons from the neutron source impinging on the neutron-activated material.

17. The method of claim 16, wherein the neutron source is a sealed neutron tube, and the neutron-activated material includes one or more components of the sealed neutron tube.

18. The method of claim 17, wherein the neutron source includes an ion source and a target configured to emit neutrons in response to ions, and the neutron-activated material is a component of the target.

19. The method of claim 11, wherein the gamma ray source is configured to emit gamma rays having an energy level that is different than an energy level of the gamma rays resulting from the interactions, and generating the pulsed neutron gamma ray spectrum and the density gamma ray spectrum includes filtering the signals according to the different energy levels.

20. The method of claim 11, wherein the plurality of selected time gates includes an inelastic gate, a thermal gate occurring after the inelastic gate and a background gate occurring after the thermal gate, and detecting the gamma rays emitted from the borehole fluid includes detecting signals during the background gate.

* * * * *